United States Patent
Goto et al.

(10) Patent No.: US 6,340,776 B2
(45) Date of Patent: Jan. 22, 2002

(54) PROCESS FOR PRODUCING 1,1,1-TRIFLUOROACETONE

(75) Inventors: Yoshihiko Goto; Ryo Nadano; Takashi Sakaya; Takayuki Nishimiya, all of Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/789,001

(22) Filed: Feb. 21, 2001

(30) Foreign Application Priority Data

Feb. 22, 2000 (JP) ............................. 12-043869
Oct. 10, 2000 (JP) ............................. 12-309649

(51) Int. Cl.$^7$ ............................................. C07C 45/63
(52) U.S. Cl. ........................ 568/394; 568/383; 568/407; 568/411; 570/176
(58) Field of Search ................................ 568/383, 407, 568/411, 394; 570/176

(56) References Cited

U.S. PATENT DOCUMENTS

| | | | |
|---|---|---|---|
| 2,917,546 A | 12/1959 | Gordon et al. | ............... 260/593 |
| 6,262,312 B1 * | 7/2001 | Goto | ........................... 568/394 |

FOREIGN PATENT DOCUMENTS

| | | |
|---|---|---|
| DE | 19620798 | 10/2000 |
| EP | 0349115 | 1/1990 |
| EP | 0598338 | 5/1994 |
| JP | 2000336057 | 12/2000 |
| JP | 2000-336057 | 12/2000 |
| WO | 97/19056 | 5/1997 |

OTHER PUBLICATIONS

Sykes et al., "A New Synthesis of Fluoro–ketones", *J. Chem. Soc.* (Lond.) 835–839 (1956).
Burdon et al., "The Sodium–Promoted Claisen Ester Condensations of Ethyl Perfluoroalkanecarboxylates", *Tetrahedron* 20:2163–2166 (1964).
Yamana et al., "A Convenient Synthesis of 2,2–difluoro enol Silyl Esthers from Chlorodifluoromethyl Ketones", *Tetrahedron Letters* vol. 24 No. 5 pp. 507–510 (1983).

* cited by examiner

*Primary Examiner*—Sreeni Padmanabhan
(74) *Attorney, Agent, or Firm*—Crowell & Moring LLP

(57) ABSTRACT

A process for producing 1,1,1-trifluoroacetone includes the step of conducting a hydrogenolysis of a halogenated trifluoroacetone, which is represented by the general formula (1), by a hydrogen gas in the presence of a catalyst containing a transition metal,

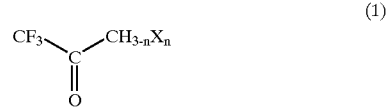

(1)

where X represents a chlorine, bromine or iodine, and n represents an integer from 1 to 3. It is possible to obtain 1,1,1-trifluoroacetone with a high yield by using the special catalyst.

15 Claims, No Drawings

PROCESS FOR PRODUCING 1,1,1-TRIFLUOROACETONE

BACKGROUND OF THE INVENTION

The present invention relates to a process for producing 1,1,1-trifluoroacetone that is useful as an intermediate of pharmaceuticals and agricultural chemicals, or as a reagent for introducing fluorine-containing groups.

1,1,1-trifluoroacetone is known to be obtained by various methods. It is described in J. Chem. Soc. (Lond.) 1956, 835 that 1,1,1-trifluoroacetone is synthesized by a Grignard reaction between trifluoroacetic acid and magnesium methyliodide. This Grignard reaction must be conducted in an anhydrous state. In addition, it is also described in Tetrahedron, 20, 2163 (1964) that trifluoroacetone can be synthesized by decarbonating trifluoroacetoethyl acetate in sulfuric acid. It is described in Tetrahedron Lett. Vol. 24 (No. 5), 507–510, 1983 that difluoromethylketones are obtained at considerably high yield as a result of reducing chlorodifluoroketones, which are represented by $CF_2ClC(=O)R$ (wherein R is a group not containing halogen) by zinc and methanol in tetrahydrofuran.

Japanese Patent Publication 2000-336057A, corresponding to Japanese Patent Application 11-147670, discloses a process for producing 1,1,1-trifluoroacetone by reacting 3,3-dichloro-1,1,1-trifluoroacetone with zinc in a solvent of a proton donor. In this process, it is necessary to have a relatively large amount of zinc.

SUMMARY OF THE INVENTION

It is an object of the present invention to provide a process for producing 1,1,1-trifluoroacetone, which is suitable for an industrial-scale production.

According to the present invention, there is provided a process for producing 1,1,1-trifluoroacetone. This process comprises conducting a hydrogenolysis of a halogenated trifluoroacetone, which is represented by the general formula (1), by a hydrogen gas in the presence of a catalyst comprising a transition metal,

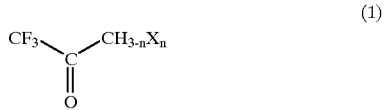

(1)

where X represents a chlorine, bromine or iodine, and n represents an integer from 1 to 3.

According to the present invention, it is possible to obtain 1,1,1-trifluoroacetone with a high yield by using the above special catalyst in hydrogenolysis of the halogenated trifluoroacetone (e.g., 3,3-dichloro-1,1,1-trifluoroacetone) by a hydrogen gas.

DESCRIPTION OF THE PREFERRED EMBODIMENTS

The hydrogenolysis can be conducted by a gas phase reaction between the halogenated trifluoroacetone (gas) and a hydrogen gas using a reactor for flow method.

The halogenated trifluoroacetone used as a starting material in the process of the present invention may be a hydrate, alcohol addition product, gem-diol, acetal or hemiacetal, or their aqueous or alcohol solutions, of a halogenated trifluoroacetone represented by the general formula (1), as indicated in the following formulas, although an aqueous solution of the hydrate is preferable due to its ease of handling:

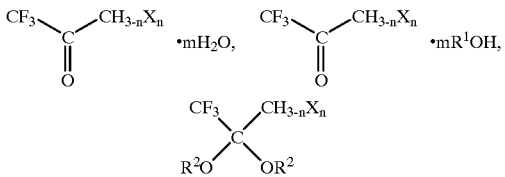

where X and n are the same as previously defined in the general formula (1), m represents an integer, $R^1$ represents an alkyl group, and each $R^2$ independently represents a hydrogen atom or alkyl group.

The halogenated trifluoroacetone can be 3-chloro-1,1,1-trifluorocetone, 3,3-dichloro-1,1,1-trifluoroacetone, or 3,3,3-trichloro-1,1,1-trifluoroacetone. These compounds can be synthesized by known processes. For example, they can be obtained by fluorinating pentachloroacetone by hydrogen fluoride in the presence of a transition metal or the like as a catalyst. Furthermore, decarboxylation of a trifluoroacetoacetic ester is known.

As stated above, the halogenated trifluoroacetone used as a starting material in the process of the present invention may be a hydrate in which a halogenated trifluoroacetone represented by the general formula (1) has hydrated to have an arbitrary number of water molecules. In the process, it is preferable to use the halogenated trifluoroacetone in the form of an aqueous solution, since its handling is easy and thereby the reaction procedures can be simplified. The existence of water is not an obstacle to the reaction, but the existence of unnecessary water is not preferable from the viewpoint of energy consumption.

As stated above, the catalyst used in the hydrogenolysis comprises a transition metal. This transition metal is preferably a noble metal such as ruthenium, palladium, platinum, iridium, and rhodium. Further examples of the transition metal other than noble metal are nickel, copper and iron. Of these, palladium and platinum are preferable. The transition metal is preferably supported on a support such as activated carbon, alumina, silica-alumina, and silica. Of these, activated carbon is preferable. It is particularly preferable to use a catalyst containing an activated carbon supporting thereon palladium or platinum. The way of making the transition metal to be supported on the support is not particularly limited. For example, it is possible to immerse a support in a solution of a transition metal compound or to spray this solution to a support, followed by drying and then reduction with hydrogen gas. The transition metal compound may be in the form of chloride, bromide, fluoride, oxide, nitrate, sulfate or carbonate. The transition metal may be in an amount of about 0.1–10 g, preferably 0.2–5 g, per 100 ml of the support. If it is less than 0.1 g, both conversion of the halogenated trifluoroacetone and yield of 1,1,1-trifluoroacetone may become too low. An amount of greater than 5 g may not be preferable from the economical viewpoint.

The reaction temperature may be 50° C. or higher, preferably 70° C. or higher, more preferably 90° C. or higher, still more preferably 100° C. or higher, further preferably 105° C. or higher. Furthermore, the reaction temperature may be 350° C. or lower, preferably 250° C. or lower, more preferably 200° C. or lower, still more preferably 150° C. or lower, further preferably 120° C. or lower. Therefore, the reaction temperature range may be 50–350° C., preferably 70–250° C., more preferably 90–120° C. If it is lower than 50° C., both conversion of the halogenated trifluoroacetone and yield of 1,1,1-trifluoroacetone may be lowered. If it is higher than 350° C., fluorine atom hydrogenolysis and/or hydrogenation of carbonyl group may proceed. With this, yield of 1,1,1-trifluoroacetone may be lowered.

The molar ratio of hydrogen (hydrogen gas) to the halogenated trifluoroacetone may be varied depending on the number of the halogen atoms (other than fluorine) of the halogenated trifluoroacetone. This ratio may be in a range of 1.5–50, preferably 2–10, more preferably 2.5–5. If it is less than 1.5, conversion of the halogenated trifluoroacetone may not be sufficiently high. Even if it is greater than 50, conversion of the halogenated trifluoroacetone may not improve further. Furthermore, this is not preferable from the economical viewpoint, due to the necessity of recovering the unreacted hydrogen gas. It is optional to make nitrogen gas coexistent with the other reagents in the reaction system in order to adjust the reaction and to suppress the catalyst deterioration.

It is preferable that the hydrogenolysis is conducted by using a reactor made of a material lined with a lining material selected from of borosilicate glasses, tetrafluoroethylene resins, chlorotrifluoroethylene resins, vinylidene fluoride resins, perfluoroalkyl vinyl ether (PFA) resins and carbon, when water exists in the reaction system. When water does not exist in the reaction system by using a halogenated trifluoroacetone that is not hydrated, it is possible to use iron, stainless steel, nickel and Hastelloy (trade name) for the reactor in addition to the above-mentioned lining material.

The way of conducting the hydrogenolysis is not particularly limited. For example, it can be conducted by the following flow method. At first, a reactor for flow method, which is resistant against the reaction conditions of the hydrogenolysis, is charged with a transition metal supported catalyst. Then, the reactor is heated from outside, and hydrogen gas is allowed to flow through a reaction tube. When the reaction tube's inside temperature reaches a predetermined temperature, the halogenated trifluoroacetone is introduced into a vaporizer for vaporizing the same and then into the reaction tube together with the hydrogen gas. A mixture of gas and/or liquid flowing out of the reaction tube is absorbed into water. Alternatively, it is cooled down and collected in the form of liquid. It is optional to separately introduce the halogenated trifluoroacetone and water into the reaction tube.

The resulting 1,1,1-trifluoroacetone can be purified by a conventional purification method used for hydrogenolysis products obtained from fluorinated compounds. For example, a reaction product containing 1,1,1-trifluoroacetone (in the form of liquid or gas), which has flowed out of the reactor together with hydrogen chloride, is cooled down. After that, hydrogen chloride is removed from the reaction product by distillation or gas-liquid phase separation. Then, the remaining acid component is removed from the product with a basic substance or the like. After that, the target product, 1,1,1-trifluoroacetone of high purity, is obtained by rectification.

The following nonlimitative catalyst preparations are illustrative of the present invention.

Catalyst Preparation 1

At first, a 200-ml eggplant-type flask was charged with 35 g of a granular activated carbon (a coconut husk carbon of a particle diameter of 4–6 mm) made by Takeda Chemical Industries, Ltd. having a trade name of GRANULAR SHIRO SAGI G2X-4/6. Then, about 120 ml of an about 20% nitric acid aqueous solution was added to the flask. After that, the flask was allowed to stand still for about 3 hr, thereby to conduct a nitric acid treatment of the activated carbon. Separately, 0.83 g of palladium (II) chloride, $PdCl_2$, was dissolved in 5 g of a 24% hydrochloric acid, to prepare a palladium chloride solution. This palladium chloride solution was poured on the activated carbon contained in the flask. Then, this flask was allowed to stand still for 2 days. Then, the activated carbon, impregnated with the palladium chloride solution, was subjected to vacuum drying with an evaporator by increasing the bath temperature to 150° C. Then, the dried activated carbon was put into a reaction tube having a diameter of 25 mm, an axial length of 400 mm, and a capacity of about 200 ml. Then, while nitrogen was allowed to flow through the reaction tube at a rate of 200–300 ml/min, the reaction tube was heated from 150° C. to 300° C. by increasing the set temperature of the reaction tube stepwise by 50° C., in order to bake the activated carbon. The reaction tube temperature was maintained at 300° C. for 1 hr in order to further bake the same, and then the set temperature was decreased to 150° C. After that, while nitrogen and hydrogen were allowed to flow therethrough at respective rates of 50 ml/min and 50 ml/min, the reaction tube temperature was increased again to 300° C. by increasing its set temperature stepwise by 30° C. for conducting reduction. With this, there was prepared a first catalyst having an activated carbon carrying thereon 0.5% of palladium, based on the weight of the activated carbon.

Catalyst Preparation 2

At first, a 200-ml eggplant-type flask was charged with 35 g of the same granular activated carbon as that of Catalyst Preparation 1. Separately, 0.46 g of hexachloroplatinic (IV) acid hexahydrate, $H_2PtCl_6.6H_2O$, was dissolved in 100 ml of 30% hydrochloric acid, to prepare a hexachloroplatinic acid solution. This solution was poured on the activated carbon contained in the flask. Then, this flask was allowed to stand still for 2 days. Then, the same procedures as those of Catalyst Preparation 1 were conducted, thereby preparing a second catalyst having an activated carbon carrying thereon 0.5% of platinum, based on the weight of the activated carbon.

The following nonlimitative examples are illustrative of the present invention.

EXAMPLE 1

At first, a tubular reactor made of glass was charged with 50 ml of the first catalyst (0.5% Pd on activated carbon) obtained in Catalyst Preparation 1. Then, the reactor was heated to 110° C., while hydrogen gas was allowed to flow through the reactor at a rate of 80 ml/min by downflow. A 3,3-dichloro-1,1,1-trifluoroacetone aqueous solution (water content: 25%) was introduced into a vaporizer at a rate of 0.2 g/min, thereby vaporizing this solution. The resulting vapor was mixed with hydrogen, and the mixture was introduced into the reactor after the reactor's inside temperature became stable. Then, the reaction was conducted for 5 hr. During the reaction, liquid and gas flowing out of the reactor were introduced into 10 g of water cooled at 0° C., thereby collecting them. The collected product in an amount of 47.2 g was found by Karl Fischer's method to contain 52.4% of water. Furthermore, it was found by gas chromatography to contain organic components of 98.4% of 1,1,1-trifluoroacetone, 0.1% of 1,1-difluoroacetone, 0.5% of 1-fluoroacetone, 0.4% of acetone and others. These percentages are areal percentages in chromatogram.

EXAMPLE 2

Example 1 was repeated except in that the flow rate of hydrogen gas was 65 ml/min, thereby collecting 53.8 g of a product. The collected product was found by Karl Fischer's method to contain 42.3% of water. Furthermore, it was found by gas chromatography to contain organic components of 97.7% of 1,1,1-trifluoroacetone, 0.4% of 1,1-difluoroacetone, 1.3% of 1-fluoroacetone, 0.3% of acetone and others.

EXAMPLE 3

Example 1 was repeated except in that the flow rate of hydrogen gas was 100 ml/min, thereby collecting 49.1 g of a product. The collected product was found by Karl Fischer's method to contain 52.8% of water. Furthermore, it was found by gas chromatography to contain organic components of 97.5% of 1,1,1-trifluoroacetone, 1.1% of 1,1-difluoroacetone, 0.5% of 1-fluoroacetone, 0.4% of acetone and others.

EXAMPLE 4

At first, a tubular reactor made of glass was charged with 50 ml of the first catalyst (0.5% Pd on activated carbon) obtained in Catalyst Preparation 1. Then, the reactor was heated to 110° C., while hydrogen gas was allowed to flow through the reactor at a rate of 80 ml/min by downflow. An aqueous solution (water content: 15%) of a raw material mixture containing 8.2% of 3-chloro-1,1,1-trifluoroacetone, 88.8% of 3,3-dichloro-1,1,1-trifluoroacetone, and 2.4% of 3,3,3-trichloro-1,1,1-trifluoroacetone was introduced into a vaporizer at a rate of 0.2 g/min, thereby vaporizing this solution. The resulting vapor was mixed with hydrogen, and the mixture was introduced into the reactor after the reactor's inside temperature became stable. Then, the reaction was conducted for 5 hr. During the reaction, liquid and gas flowing out of the reactor were introduced into 20 g of water cooled at 0° C., thereby collecting them. The collected product in an amount of 56.9 g was found by Karl Fischer's method to contain 45.6% of water. Furthermore, it was found by gas chromatography to contain organic components of 97.9% of 1,1,1-trifluoroacetone, 0.4% of 1,1-difluoroacetone, 0.5% of 1-fluoroacetone, 0.6% of acetone and others.

EXAMPLE 5

Example 1 was repeated except in that the first catalyst was replaced with the second catalyst (0.5% Pt on activated carbon) obtained in Catalyst Preparation 2 and that the water cooled at 0° C. was in an amount of 14 g, thereby collecting 64.2 g of a product. The collected product was found by Karl Fischer's method to contain 46.3% of water. Furthermore, it was found by gas chromatography to contain organic components of 99.0% of 1,1,1-trifluoroacetone, 0.1% of 1,1-difluoroacetone, 0.1% of 1-fluoroacetone, 0.3% of acetone and others.

EXAMPLE 6

At first, a tubular reactor made of glass was charged with 500 ml of the first catalyst (0.5% Pd on activated carbon) obtained in Catalyst Preparation 1. Then, the reactor was heated to 95° C., while hydrogen gas was allowed to flow through the reactor at a rate of 500 ml/min by downflow. A raw material mixture containing 9.6% of 3-chloro-1,1,1-trifluoroacetone, 84.0% of 3,3-dichloro-1,1,1-trifluoroacetone, and 3.9% of 3,3,3-trichloro-1,1,1-trifluoroacetone was introduced into a vaporizer at a rate of 1.5 g/min, thereby vaporizing the mixture. The resulting vapor was mixed with hydrogen, and the mixture was introduced into the reactor after the reactor's inside temperature became stable. Then, the reaction was conducted for 6 hr. During the reaction, liquid and gas flowing out of the reactor were introduced into 500 g of water cooled at 0° C., thereby collecting them. The collected product in an amount of 909 g was found by Karl Fischer's method to contain 55.0% of water. Furthermore, it was found by gas chromatography to contain organic components of 98.1% of 1,1,1-trifluoroacetone, 0.7% of 1,1-difluoroacetone, and others.

EXAMPLE 7

At first, a tubular reactor made of glass was charged with 10 ml of the second catalyst (0.5% Pt on activated carbon) obtained in Catalyst Preparation 2. Then, the reactor was heated to 110° C., while hydrogen gas was allowed to flow through the reactor at a rate of 80 ml/min by downflow. An aqueous solution (water content: 15%) of a raw material mixture containing 8.2% of 3-chloro-1,1,1-trifluoroacetone, 88.8% of 3,3-dichloro-1,1,1-trifluoroacetone, and 2.4% of 3,3,3-trichloro-1,1,1-trifluoroacetone was introduced into a vaporizer at a rate of 0.16 g/min, thereby vaporizing the mixture. The resulting vapor was mixed with hydrogen, and the mixture was introduced into the reactor after the reactor's inside temperature became stable. Then, the reaction was conducted for 1 hr. During the reaction, liquid and gas flowing out of the reactor were introduced into 10 g of water cooled at 0° C., thereby collecting them. The collected product in an amount of 16.1 g was found by Karl Fischer's method to contain 61.2% of water. Furthermore, it was found by gas chromatography to contain organic components of 96.7% of 1,1,1-trifluoroacetone, 1.5% of 3-chloro-1,1,1-trifluoroacetone, and others.

EXAMPLE 8

At first, a tubular reactor made of glass was charged with 50 ml of the second catalyst (0.5% Pt on activated carbon) obtained in Catalyst Preparation 2. Then, the reactor was heated to 110° C., while hydrogen gas was allowed to flow through the reactor at a rate of 80 ml/min by downflow. 3,3-dichloro-1,1,1-trifluoroacetone was introduced into a vaporizer at a rate of 0.18 g/min, thereby vaporizing this compound. The resulting vapor was mixed with hydrogen, and the mixture was introduced into the reactor after the reactor's inside temperature became stable. Then, the reaction was conducted for 1 hr. During the reaction, liquid and gas flowing out of the reactor were introduced into 10 g of water cooled at 0° C., thereby collecting them. The collected product in an amount of 17.4 g was found by Karl Fischer's method to contain 55.9% of water. Furthermore, it was found by gas chromatography to contain organic components of 95.4% of 1,1,1-trifluoroacetone, 3.0% of 3-chloro-1,1,1-trifluoroacetone, and others.

The entire disclosure of each of Japanese Patent Applications No. 2000-043869 filed on Feb. 22, 2000 and No. 2000-309649 filed on Oct. 10, 2000, including specification, claims and summary, is incorporated herein by reference in its entirety.

What is claimed is:

1. A process for producing 1,1,1-trifluoroacetone, comprising conducting a hydrogenolysis of a halogenated trifluoroacetone, which is represented by the general formula (1), by a hydrogen gas in the presence of a catalyst comprising a transition metal,

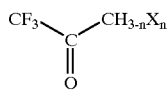 (1)

where X represents a chlorine, bromine or iodine, and n represents an integer from 1 to 3.

2. A process according to claim 1, wherein said transition metal is selected from the group consisting of ruthenium, palladium, platinum, iridium, rhodium, nickel, copper, and iron.

3. A process according to claim 2, wherein said transition metal is selected from the group consisting of ruthenium, palladium, platinum, iridium, and rhodium.

4. A process according to claim 1, wherein said catalyst further comprises a support supporting thereon said transition metal.

5. A process according to claim 4, wherein said support is selected from the group consisting of activated carbon, alumina, silica-alumina, and silica.

6. A process according to claim 5, wherein said support is activated carbon supporting thereon said transition metal that is palladium or platinum.

7. A process according to claim 4, wherein said transition metal is in an amount of 0.1–10 g per 100 ml of said support.

8. A process according to claim 1, wherein said hydrogenolysis is conducted in the presence of water.

9. A process according to claim 1, wherein a hydrate of said halogenated trifluoroacetone is used as a raw material for conducting said hydrogenolysis.

10. A process according to claim 1, wherein an aqueous solution of a hydrate of said halogenated trifluoroacetone is used as a raw material for conducting said hydrogenolysis.

11. A process according to claim 1, wherein an aqueous solution of said halogenated trifluoroacetone is used as a raw material for conducting said hydrogenolysis.

12. A process according to claim 1, said hydrogenolysis is conducted by a gas phase reaction.

13. A process according to claim 1, wherein said halogenated trifluoroacetone is selected from the group consisting of 3-chloro-1,1,1-trifluoroacetone, 3,3-dichloro-1,1,1-trifluoroacetone, and 3,3,3-trichloro-1,1,1-trifluoroacetone.

14. A process according to claim 1, wherein said hydrogenolysis is conducted at a temperature of 50–350° C.

15. A process according to claim 1, wherein a molar ratio of said halogenated trifluoroacetone to said hydrogen gas is 1.5 to 50.

* * * * *